United States Patent [19]

Tan

[11] 4,347,852
[45] Sep. 7, 1982

[54] HEARTBEAT SENSOR HOLDING DEVICE

[76] Inventor: Josef K. S. Tan, 1891 Hillcrest Ave., St. Paul, Minn. 55116

[21] Appl. No.: 150,712

[22] Filed: May 19, 1980

[51] Int. Cl.³ .............................................. A61B 5/02
[52] U.S. Cl. .................................................. 128/687
[58] Field of Search ............... 128/632, 644, 665–667, 128/687–690, 77, 87 A; DIG. 24/17, 29; 224/217; 434/166

[56] References Cited

U.S. PATENT DOCUMENTS

| 1,174,887 | 3/1916 | Meriwether | 224/217 |
| 2,528,456 | 10/1950 | Stevenson | 128/87 A |
| 3,107,664 | 10/1963 | Smith | 128/687 |
| 3,450,133 | 6/1969 | Birch | 128/644 |
| 3,482,565 | 12/1969 | Gowen | 128/667 |

FOREIGN PATENT DOCUMENTS 2635221  2/1978  Fed. Rep. of Germany ...... 128/666

OTHER PUBLICATIONS

Smith, E. W. et al., "Treatment of Mallet Finger", Jrnl. of Bone & Joint Surgery, Apr. 1946, p. 394.
Edwards, J. W., "Splints for the Hand", *Orthopedic Appliance Atlas*, vol. 1, p. 305, 1952.

*Primary Examiner*—Kyle L. Howell
*Assistant Examiner*—Francis J. Jaworski
*Attorney, Agent, or Firm*—Freilich, Hornbaker, Wasserman, Rosen & Fernandez

[57] ABSTRACT

A device for holding a heartbeat sensor in a relatively fixed relationship with respect to the end of a user's fingertip. More particularly, a device is disclosed wherein a single sheet of resilient material is formed into a base portion for holding the heartbeat sensor and three resilient bands that extend upwardly therefrom. The bands are adapted to grip the user's fingertip. In one embodiment of the invention, the bands and base portion define a U-shaped channel of constant cross-sectional area. In this embodiment a holding structure for the heartbeat sensor is wedge-shaped, the wedge-shaped holding structure being adapted to be held by the base portion so that the cross-sectional area defined by each band and the wedge-shaped holding structure decreases along the longitudinal length of the base portion. In another embodiment of the invention, each band defines a smaller cross-sectional area with respect to the base portion. Thus both embodiments result in more pressure being applied to the sensor at the portion of the user's fingertip closest to the end.

19 Claims, 7 Drawing Figures

HEARTBEAT SENSOR HOLDING DEVICE

FIELD OF THE INVENTION

The invention relates to portable heartbeat sensors attachable to a user's fingertip for providing a heartbeat signal as the user exercises.

BACKGROUND OF THE INVENTION

Portable exercise monitoring devices are becoming increasingly popular as the public becomes aware of the value of periodic exercise activities. However, for many exercisers it is essential that exercise activities not be overdone. For example, it is important for an exerciser having a heart difficulty to have his heartbeat rate monitored during exercise. Various exercise monitoring devices are in existence for alerting a user that a predetermined heartbeat rate has been exceeded. Once such device is disclosed in my U.S. patent application Ser. No. 103,422. One problem with heartbeat sensors such as that described in the referenced patent application is if the sensor moves relative to a fixed position on the user's body, the heartbeat measured thereby becomes somewhat blurred and ambiguous. Thus, the actual time of occurrence of the heartbeat and the isolation of the various portions of a single heartbeat cycle becomes difficult. It is important that small portable heartbeat sensors maintain a fixed relationship with respect to the monitoring area on the user's body. A typical exercise monitoring device uses the user's fingertip as the monitoring point, and attempts to maintain the heartbeat sensor in a fixed relationship with respect to an area located underneath a lower portion of the user's fingertip as the user exercises. Several devices designed to accomplish that purpose are disclosed in the referenced patent application. Although those devices have been found to be satisfactory, the device provided by the present invention is a one-piece device which can be quickly and accurately positioned on the user's fingertip while at the same time being extremely compact and simple in design.

SUMMARY OF THE INVENTION

The invention provides a device for holding a heartbeat sensor in a relatively fixed relationship with respect to a user's fingertip. The device includes a base portion for holding the heartbeat sensor, and a pressure producing means connected to the base portion for holding the user's fingertip against the heartbeat sensor, the pressure producing means including means for causing pressure between the heartbeat sensor and the user's fingertip to be greater at the portion of the user's fingertip closest to the end than at the portion of the user's fingertip furthest from the end.

In a specific embodiment of the invention, a single sheet of resilient material is formed into a base portion and three flexible bands extending upwardly and over the base portion. Each of the bands partially forms an arch with respect to the base portion and is adapted to grip a portion of the user's fingertip. A holding structure for the heartbeat sensor is also provided, the holding structure being in the form of a wedge having its thickest portion closest to the end of the user's fingertip. The holding structure is adapted to be held by the base portion. In a further embodiment of the invention, a single strip of material is again formed into a base portion and three upwardly extending bands, each band defining a smaller cross-sectional area along a longitudinal length of the base portion. A holding structure for the heartbeat sensor is adapted to be held by the base portion. The user's fingertip is located between the bands and the base portion so that the fingertip end is gripped by the band defining the smallest cross-sectional area. The two embodiments above described thus effect a maximum pressure on the portion of the fingertip closest to its end rather than on the portion of the fingertip furthest from its end. The holding structure is adapted to position the heartbeat sensor at the maximum pressure portion, thereby minimizing movement between the sensor and the fingertip.

DETAILED DESCRIPTION

Detailed illustrative embodiments of the invention disclosed herein exemplify the invention and are currently considered to be the best embodiments for such purposes. They are provided by way of illustration not limitation of the invention. Various modifications thereof will occur to those skilled in the art, and such modifications are within the scope of the claims which define the present invention.

As previously explained, a device for holding a heartbeat sensor against a user's fingertip is disclosed wherein a pressure producing means in the form of three resilient bands is attached to a base portion which is adapted to hold the heartbeat sensor and an associated holding structure. The bands and sensor holding structure are configured so that more pressure is applied between the end of the user's fingertip and the holding structure than at the portions of the fingertip further from the end. The heartbeat sensor is located with respect to the holding structure so that it is located near the area of maximum pressure. The locating of the sensor near the maximum pressure area tends to maintain the sensor in a fixed relationship with respect to the user's fingertip during exercise activities. In one of two embodiments of the invention disclosed below, the heartbeat sensor is mounted in a wedge-shaped holding structure having its thickest portion closest to the end of the user's fingertip, thereby resulting in increased pressure between the holding structure and the fingertip in the portion closest to its end. In another embodiment of the invention, the sensor holding structure for the heartbeat sensor is not wedge-shaped. The bands extending from the base portion are formed to define successively smaller cross-sectional areas. Thus, as the user's fingertip is inserted into a volume defined by the bands, increased pressure is applied to the portion of the fingertip closest to its end, thereby tending to maintain a fixed relationship between the heartbeat sensor and the user's fingertip.

Figure 1:
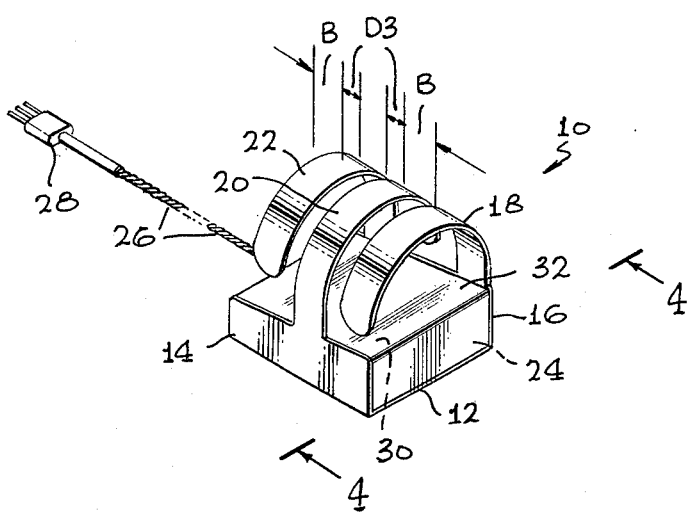
FIG. 1 is a perspective view of one embodiment of a heartbeat sensor holding device provided by the invention.

Referring now to FIG. 1, a heartbeat sensor holding device 10 includes a base portion 12, a first sidewall portion 14, a second sidewall portion 16 and first, second and third bands 18, 20 and 22, respectively, all of which are formed from a single sheet of material. The second band 20 extends from the first sidewall portion 14 and the first and third bands 18 and 22 extend from the second sidewall portion 16. A wedge-shaped sensor holding structure 24 is provided, a top portion of which is adapted to hold the heartbeat sensor as will be described below. Leads 26 from the heartbeat sensor terminate in a plug 28 which is suitable for interfacing the sensor with an appropriate monitoring device. Although the bands 18, 20, and 22 are shown formed from the same sheet of material as the base and sidewall portions 12, 14, and 16, it should be understood that the bands could be formed of a different material and attached to the sidewall portions 14 and 16 or directly to the base portion 12. The bands are formed from resilient material which is deformable so as to grip the user's fingertip when inserted into a U-shaped channel defined by the bands and wedge-shaped holding structure 24. In the embodiment shown in FIG. 1, the distance between the highest point of each of the bands 18, 20 and 22 with respect to the base portion 12 is the saame. However, because of the wedge-shaped holding structure 24, the cross-sectional area defined by each band and the holding structure 24 is smallest for the first band 18 and largest for the third band 22. Thus, the bands 18, 20 and 22 in conjunction with an upper surface 30 of the holding structure 24 define a funnel-shaped volume of decreasing cross-sectional area. Exposed surfaces of the wedge-shaped holding structure 24 are covered with a thin sheet of plastic material 32 which protects the heartbeat sensor held by the holding structure 24 from moisture, dust, and the like.

Figure 2:
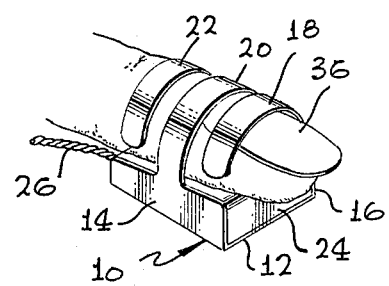
FIG. 2 is a perspective view of the holding device of FIG. 1 positioned on a user's fingertip.

In FIG. 2, the heartbeat sensor holding device 10 can be seen mounted on a user's fingertip 36. Fingertip as used herein is defined as that protion of a finger extending from the last knuckle to the end of the finger. The end portion of the fingertip is defined as that portion of the fingertip that is generally below the fingernail. As can be seen, the bands 18, 20 and 22, being formed of a resilient material, grip the user's fingertip when it is located within the funnel-shaped volume defined by the bands and the wedge-shaped holding structure 24. As can be appreciated, the greatest pressure between the fingertip 36 and the holding structure 24 occurs between the end portion of the fingertip and the end portion of the holding structure 24. The portion of the holding structure 24 underneath the first band 18 tends to remain relatively fixed with respect to the user's fingertip and any movement between the fingertip 36 and the holding structure 24 tends to be greatest in the area of the holding structure 24 under the third band 22. Thus, as the user exercises, a signal sensed by a heartbeat sensor directly underneath the first band 18 tends to be more precisely related to the beat of the user's heart rather than to movements of the heartbeat sensor with respect to the user's fingertip.

Figure 3:
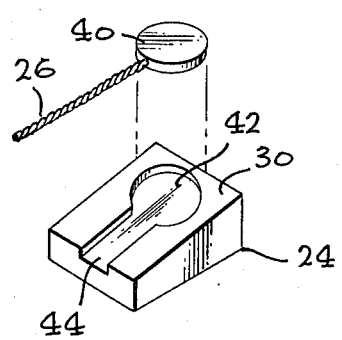
FIG. 3 is a perspective view of a heartbeat sensor holding structure and its associated heartbeat sensor.

The wedge-shaped holding structure 24 is shown in FIG. 3. The structure 24 is adapted to receive a heartbeat sensor 40 which could be of several types including a pressure sensing transducer or a light-measuring device having an output signal related to changes in the volume of blood within the user's fingertip. The upper surface 30 of the holding structure 24 has a depression 42 formed therein for receiving the heartbeat sensor 40 and a channel 44 for receiving the leads 26. The depression 42 is located with respect to the upper surface 30 so that it is positioned below the first band 18, thereby locating the sensor 40 in an area of maximum pressure between the fingertip 36 and the holding structure 24.

Figure 4:
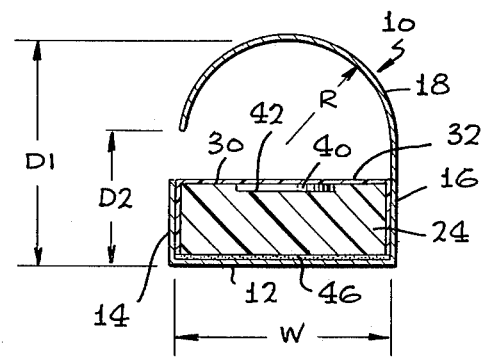
FIG. 4 is a cross-sectional view taken along line 4—4 of FIG. 1.

Referring now to FIG. 4, a cross-sectional view of the heartbeat sensor holding device 10 taken along line 4—4 of FIG. 1 showing the first band 18, the first sidewall portion 14, the second sidewall portion 16 and the base portion 12 can be seen. The holding structure 24 is attached to the base portion 12 by a suitable adhesive 46. The depression 42 and the heartbeat sensor 40 can also be seen. As previously explained, the heartbeat sensor 40 and holding structure 24 are covered by the thin sheet of plastic material 32. In this embodiment, the single sheet of material utilized to form the bands and the sidewall and base portions is aluminum 3003 H14 0.016 inches thick. The distance D1 between the top of each band and the base portion 12 is 9/16 inch, and the distance D2 between the unattached ends of the first and third bands 18 and 22 and the base portion is approximately 0.32 inches. The radius R of the curved portion of each band is 5/16 inch. The width of the base portion W is 0.635 inches and the width of each of the bands B as shown in FIG. 1 is 0.20 inches. The distance D3 between each band is 0.08 inches. The wedge-shaped holding structure 24 is approximately 0.31 inches high at its thickest end and approximately 0.19 inches high at its thinnest end. It has been empirically found that a heartbeat sensor holding device having the dimensions previously described and formed of the aluminum material identified above maintains a substantially fixed relationship between the user's fingertip end portion and the heartbeat sensor 40.

Figure 5:
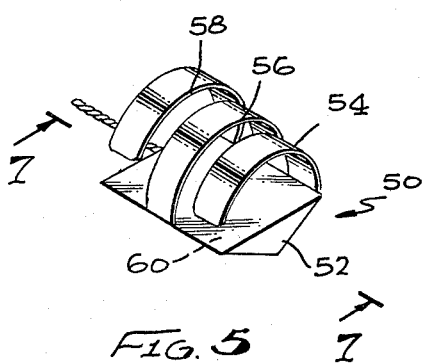
FIG. 5 is a perspective view of a further embodiment of the heartbeat sensor holding device provided by the invention.
Figure 6:
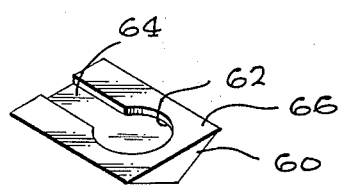
FIG. 6 is a perspective view of the heartbeat sensor holding structure for the embodiment shown in FIG. 5.
Figure 7:
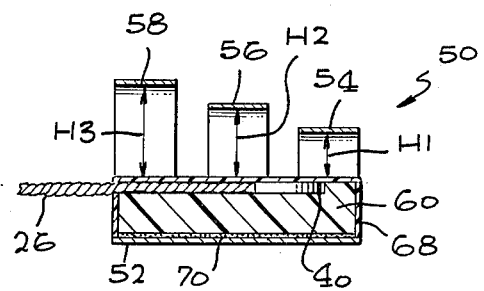
FIG. 7 is a cross-sectional view taken along line 7—7 of FIG. 5.

A further embodiment of the invention is shown in FIG. 5. Here, the heartbeat sensor holding device 50 has a triangularly-shaped base portion 52 and first, second and third bands 54, 56, and 58 extending upwardly therefrom. In FIG. 6 a sensor holding structure 60 is provided, the structure 60 having a depression 62 and channel 64 formed in its upper surface 66 for containing the heartbeat sensor 40 and associated leads 26 shown in FIG. 3. The holding structure 60 is formed so as to be contained by the triangularly-shaped base portion 52 shown in FIG. 5. A cross-sectional view taken along the lines 7—7 of FIG. 5 is shown in FIG. 7. Here, the base portion 52, sensor holding structure 60, sensor 40, and leads 26 can be seen. The sensor holding structure 60, sensor 40 and leads 26 are covered with a plastic sheet 68, as in the first embodiment, in order to protect the sensor 40 from moisture, dust and the like. The plastic sheet 68 and the sensor holding structure 60 are attached to the base portion 52 by a suitable adhesive 70. As can be seen in FIG. 7, the closer a band is to the end portion of the user's fingertip, the closer a top portion of the band is to the top of the sensor holding structure 60 as shown at H1, H2, and H3. Thus, as the user's fingertip is inserted into the funnel-shaped channel defined by the bands 54, 56 and 58, and the holding structure 60, the end portion of the fingertip will experience the greatest pressure due to H1 being the smallest at that point. Thus, maximum pressure is exerted on the heartbeat sensor 40 by the fingertip portion directly below the first band 54. In the first embodiment, increased pressure is provided at the fingertip end portion because of the wedge-shaped holding structure 24, whereas in the second embodiment, increased pressure is provided by the band 54 closest to the holding structure 60. Although the two embodiments are similar in function, the second embodiment provides a slightly more compact heartbeat sensor holding device than the first embodiment.

Thus, as can be appreciated, a heartbeat sensor holding device has been described wherein a relatively fixed relationship can be maintained between a user's fingertip and a heartbeat sensor by providing increased pressure between the heartbeat sensor and the fingertip portion directly above the heartbeat sensor.

What is claimed is:

1. A device for holding a heartbeat sensor in a relatively fixed relationship with respect to a user's fingertip, comprising:
   a heartbeat sensor
   a sensor holding structure for holding said sensor;
   a base portion for holding said holding structure with said heartbeat sensor; and
   pressure producing means connected to said base portion for holding said user's fingertip against said heartbeat sensor, said pressure producing means comprising means for causing pressure between said heartbeat sensor and said user's fingertip to be greater at the portion of said user's fingertip closest to the end than at the portion of said user's fingertip farthest from the end, said sensor being contained in a wedge-shaped holding structure adapted to be held by said base portion, said holding structure having a wedge-shaped top side at which said sensor is exposed, so that the thickest portion of said holding structure is closest to the end of said user's fingertip.

2. The device of claim 1 wherein said base portion comprises sidewalls, said pressure producing means further comprising a plurality of deformable resilient bands each of which is connected at one end to one of said base portion sidewalls, said bands being adapted to releasably grip a user's fingertip when positioned in a channel defined by said bands and said wedge-shaped holding structure.

3. The device of claim 2 wherein said bands and said sidewalls define a first U-shaped channel having a substantially constant cross-sectional area along its length, and said wedge-shaped holding structure, when positioned in said base portion, and in conjunction with said bands, define a second U-shaped channel having a diminishing cross-sectional area along the length of said second channel whereby when said user's fingertip is positioned in said channel, more pressure is applied between said user's finger and said holding structure at the portion of said user's fingertip closest to the end.

4. The device of claim 3 wherein said plurality of bands comprises three bands, a middle one of which is connected to one of said sidewalls and the other two are connected to another of said sidewalls.

5. The device of claim 3 wherein said bands and said base portion are a one-piece element formed from a single sheet of material.

6. The device of claim 5 wherein said single sheet of material is formed of aluminum 3003 H14, 0.016 inches thick.

7. The device of claim 1 wherein said pressure-producing means further comprises a plurality of deformable resilient bands each of which is connected to said base portion, said bands being adapted to releasably grip a user's finger by surrounding said finger, when located in a channel defined by said bands and said holding structure.

8. The device of claim 7 wherein said bands and said sensor holding structure when held by said base portion define a U-shaped channel having a diminishing cross-sectional area along the length of said channel whereby when said user's fingertip is positioned in said channel, more pressure is applied between said user's fingertip and said holding structure at the end portion of said user's fingertip.

9. The device of claim 8 wherein said bands and said holding structure define a diminishing cross-sectional area along the length of said U-shaped channel.

10. The device of claim 8 wherein said bands and said base portion define a diminishing cross-sectional area along the length of said U-shaped channel.

11. The device of claim 10 wherein said plurality of bands comprises three bands.

12. The device of claim 11 wherein said bands and said base portion are a one-piece element formed from a single sheet of material.

13. A device for holding a heartbeat sensor in a relatively fixed relationship to a user's fingertip, comprising:
   a one-piece element made of a single sheet of material formed into a base portion and a plurality of flexible bands extending upwardly and over said base portion, each of said bands extending upwardly and over said base portion, each of said bands partially forming an arch with respect to said base portion and adapted to grip the end of said user's fingertip; and
   a holding structure for holding said heartbeat sensor, said holding structure adapted to be held within a volume partially defined by said base portion, each of said bands partially forming an arch with respect to said base portion and adapted to grip the end of said user's fingertip; and
   a holding structure for holding said heartbeat sensor, said holding structure adapted to be held within a volume partially defined by said base portion, said holding structure and said bands being adapted to grip said user's fingertip so that more pressure is applied between the user's fingertip and said holding structure at the end portion of the user's fingertip than at other portions.

14. The device of claim 13 wherein said holding structure is wedge-shaped and located within said base portion so that the thickest portion is closest to the end of said user's fingertip, thereby resulting in the pressure between said user's fingertip and said holding structure being related to the distance from the end of said user's fingertip.

15. The device of claim 14 wherein said plurality of bands comprises three bands.

16. The device of claim 13 wherein said bands define arches having successively smaller cross-sectional areas, the smallest cross-sectional area being that closest to the end of said user's fingertip, thereby resulting in the pressure between said user's fingertip and said holding structure being related to the distance from the end of said user's fingertip.

17. The device of claim 16 wherein said plurality of bands comprises three bands.

18. A device for holding a heartbeat sensor in a relatively fixed relationship to an end portion of a user's fingertip, comprising:
- longitudinally-extending holding means defining sidewalls and a top side which is wedge-shaped along the length of said holding means, for containing said heartbeart sensor so that it is exposed on said wedge-shaped top side; and
- a plurality of resilient arch-shaped gripping bands each of which is connected at one end to one of said sidewalls along the longitudinal dimension of said holding means whereby the cross-sectional area defined by each arch with respect to said holding means becomes successively smaller, said arches being adapted to receive the end portion of said user's fingertip so that the end portion of said fingertip is closest to said arch defining the smallest cross-sectional area.

19. The device of claim 18 wherein said plurality of bands comprise three bands.